(12) United States Patent
Cummins et al.

(10) Patent No.: US 11,690,652 B1
(45) Date of Patent: Jul. 4, 2023

(54) MODULAR SCREW ASSEMBLY

(71) Applicant: Zavation Medical Products, LLC, Flowood, MS (US)

(72) Inventors: John Franklin Cummins, Kosciusko, MS (US); John Lawrence Walker, Madison, MS (US)

(73) Assignee: ZAVATION MEDICAL PRODUCTS LLC, Flowood, MS (US)

( * ) Notice: Subject to any disclaimer, the term of this patent is extended or adjusted under 35 U.S.C. 154(b) by 0 days.

(21) Appl. No.: 17/889,977

(22) Filed: Aug. 17, 2022

(51) Int. Cl.
*A61B 17/70* (2006.01)
*A61B 17/00* (2006.01)

(52) U.S. Cl.
CPC ...... *A61B 17/7032* (2013.01); *A61B 17/7037* (2013.01); *A61B 2017/00862* (2013.01)

(58) Field of Classification Search
CPC .............. A61B 17/7032; A61B 17/7035–7037
See application file for complete search history.

(56) References Cited

U.S. PATENT DOCUMENTS

| | | | |
|---|---|---|---|
| 5,476,464 A | 12/1995 | Metz-Stavenhagen et al. |
| 5,733,286 A | 3/1998 | Errico et al. |
| 6,248,105 B1 | 6/2001 | Schläipfer et al. |
| RE37,665 E | 4/2002 | Ralph et al. |
| 6,918,911 B2 | 7/2005 | Biedermann et al. |
| 7,141,051 B2 | 11/2006 | Janowski et al. |
| 7,335,202 B2 | 2/2008 | Matthis et al. |
| 7,503,924 B2 | 3/2009 | Lee et al. |
| 7,530,992 B2 | 5/2009 | Biedermann et al. |
| 7,766,945 B2 | 8/2010 | Nilsson et al. |
| 8,034,086 B2 | 10/2011 | Iott et al. |
| 8,048,112 B2 | 11/2011 | Suzuki et al. |
| 8,062,339 B2 | 11/2011 | Hammer et al. |
| 8,075,590 B2 | 12/2011 | Janowski et al. |
| 8,172,876 B2 | 5/2012 | Janowski et al. |
| 8,192,470 B2 | 6/2012 | Biedermann et al. |
| 8,221,472 B2 | 7/2012 | Peterson et al. |
| 8,343,165 B2 | 1/2013 | Berrevoets |
| 8,475,495 B2 | 7/2013 | Iott et al. |
| 8,617,217 B2 | 12/2013 | Iott et al. |
| 8,632,571 B2 | 1/2014 | Kraus |
| 8,709,051 B2 | 4/2014 | Hammer et al. |
| 8,740,946 B2 | 6/2014 | Peterson et al. |
| 8,790,374 B2 | 7/2014 | Iott et al. |
| 8,894,691 B2 | 11/2014 | Iott et al. |
| 8,940,024 B2 | 1/2015 | Biedermann et al. |
| 8,951,290 B2 | 2/2015 | Hammer et al. |
| 9,005,260 B2 | 4/2015 | Dauster et al. |
| 9,138,262 B2 | 9/2015 | Iott et al. |
| 9,179,937 B2 | 11/2015 | Iott et al. |
| 9,259,254 B2 | 2/2016 | Iott et al. |
| 9,289,246 B2 | 3/2016 | Biedermann et al. |
| 9,375,236 B2 | 6/2016 | Hammer et al. |

(Continued)

*Primary Examiner* — Eduardo C Robert
*Assistant Examiner* — Michelle C Eckman
(74) *Attorney, Agent, or Firm* — IP & T Group LLP

(57) ABSTRACT

A modular screw assembly for use in stabilizing a spinal column. The assembly has a fastener which couples to a screw head of a bone anchor, a screw head coupler, a retaining ring, and a friction ring. The fastener houses the screw head coupler, the retaining ring, and the friction ring. Translation of the fastener by the screw head results in the retaining ring elastically deforming and then snapping around the screw head.

21 Claims, 8 Drawing Sheets

(a)   (b)   (c)   (d)   (e)

(56) References Cited

U.S. PATENT DOCUMENTS

| | | |
|---|---|---|
| 9,439,682 B2 | 9/2016 | Iott et al. |
| 9,439,700 B2 | 9/2016 | Peterson et al. |
| 9,463,048 B2 | 10/2016 | Iott et al. |
| 9,750,542 B2 | 9/2017 | Iott et al. |
| 9,848,892 B2 | 12/2017 | Biedermann et al. |
| 9,936,979 B2 | 4/2018 | Peterson et al. |
| 9,949,766 B2 | 4/2018 | Iott et al. |
| 10,070,897 B1 | 9/2018 | Gregory et al. |
| 10,105,162 B2 | 10/2018 | Kim |
| 10,194,947 B2 | 2/2019 | Hammer et al. |
| 10,299,834 B2 | 5/2019 | Iott et al. |
| 10,524,839 B2 | 1/2020 | Ahn |
| 10,716,596 B2 | 7/2020 | Gregory et al. |
| 11,020,150 B1* | 6/2021 | Doubler ............. A61B 17/7032 |
| 11,051,855 B2 | 7/2021 | Iott et al. |
| 2008/0015579 A1* | 1/2008 | Whipple ............ A61B 17/7037 606/250 |
| 2009/0143827 A1* | 6/2009 | Levy ................. A61B 17/7037 606/301 |
| 2013/0018428 A1* | 1/2013 | Harper ............... A61B 17/8685 606/305 |
| 2013/0218213 A1* | 8/2013 | Lemoine ........... A61B 17/7032 606/305 |
| 2015/0196338 A1* | 7/2015 | Biedermann ...... A61B 17/8605 606/305 |
| 2016/0183982 A1* | 6/2016 | Bazille .............. A61B 17/7035 606/266 |
| 2017/0281241 A1* | 10/2017 | Jackson ............ A61B 17/7037 |
| 2019/0183536 A1* | 6/2019 | May ................... A61B 17/7037 |
| 2020/0337858 A1* | 10/2020 | Santiago .............. A61F 2/4611 |

* cited by examiner

MODULAR SCREW ASSEMBLY

BACKGROUND OF THE INVENTION

Field of the Invention

The present invention relates to a system (including a screw and rod assembly) for stabilizing the spinal column.

Description of the Related Art

Disorders of the bone include disorders such as for example degenerative disc disease, disc herniation, osteoporosis, spondylolisthesis, stenosis, scoliosis (and other curvature abnormalities), kyphosis, tumor, fracture, arthritis, calcification, etc. Such disorders may result from factors including trauma, disease and degenerative conditions caused by injury and aging.

Bone disorders typically result in symptoms including pain, nerve damage, and partial or complete loss of mobility. Additionally, severe pain and discomfort can occur due to the pressure exerted by bones on nerves.

In the field of medical implant devices, screws are often used to position stabilizing connecting rods in place between vertebra. For example, when a vertebra (that is no longer functional for example due to an intervertebral disk defect) is to be fixed to adjacent vertebrae, two connection rods are secured to the vertebrae in question with the aid of pedicle screws, with a lateral spacing being maintained between the pedicle screws.

The following provides a non-exhaustive list of stabilizing systems and devices known in the art.

U.S. Pat. No. 8,062,339 (the entire contents of which are incorporated herein by reference) describes a system for connecting a fastener element (e.g., a pedicle screw) relative to a rod for the purposes of vertebral fixation. The system in the '339 patent permits multi-axial movement between the fastener element and the rod. The system in the '339 patent permits the angular relationship between the fastener element and the rod to be held in a desired orientation.

U.S. Pat. No. 6,918,911 (the entire contents of which are incorporated herein by reference) describes a receiver part for articulated connection of a bone anchoring element with a rod. The bone anchoring element in the '911 patent has a shank part and a head. The receiver part includes a first end and a second end opposite the first end. A bore extends from the first end in the direction of the second end for guiding through the shank part. Adjacent to the bore is a section for receiving the head. An opening extends from the second end in the direction of the first end for inserting the shank part with head. A recess extends from the second end in the direction of the first end for forming a channel with a bottom for receiving the rod, forming two open legs.

U.S. Pat. No. 7,335,202 (the entire contents of which are incorporated herein by reference) describes an implant having a shaft and a holding element connected therewith for connecting with a rod. A recess is provided in the holding element that includes a U-shaped cross section for accommodation of the rod and two free legs at one end which include an inner thread. A closure element fixes the rod inserted into the U-shaped recess. The closure element has an outer thread cooperating with the inner thread of the legs. An abutment at or in the holding element limits tilting of the closure element about the rod at the time of final tightening of the closure element in the holding element.

U.S. Pat. No. 8,221,472 (the entire contents of which are incorporated herein by reference) describes a bone anchor for attaching a rod to a bone. The bone anchor has an anchor member for attachment to the bone and an anchor head having a U-shaped opening for receiving the rod. The bone anchor in the '472 patent also includes a locking cap having a main body and a set screw.

U.S. Pat. No. 8,048,112 (the entire contents of which are incorporated herein by reference) describes a fixing apparatus including a pressure fixing device to pressure fix a rod to a circular arc rod engagement portion. There are small protruding portions that bite into the rod. A recess surface of the circular arc rod engagement portion between the small protruding portions is formed as a rough surface.

U.S. Pat. No. 7,766,945 (the entire contents of which are incorporated herein by reference) describes a stabile construct to facilitate connecting a spinal fixation rod to a plurality of vertebral bodies. The construct or implant of the '945 patent had a housing and an insert. The housing and insert were shaped to cooperatively engage the bone screw and rod to provide for polyaxial orientation between the bone screw and the remainder of the construct.

U.S. Pat. No. 8,034,086 (the entire contents of which are incorporated herein by reference) describes a spinal fixation system whereby a coupling element allows a physician to selectively lock or unlock either a) the connection between the coupling element and a fastener, such as to allow for repositioning of the coupling element orb) the connection between the coupling element and an elongate rod.

U.S. Pat. No. 8,192,470 (the entire contents of which are incorporated herein by reference) describes a bone anchoring device including a) a bone anchoring element having a shaft for anchoring in the bone and a head and b) a receiving part for coupling a rod to the bone anchoring element. The receiving part in the '470 patent includes a first portion with a first end and a second end and a U-shaped recess for receiving the rod, the recess extending from the first end in the direction of the second end thereby forming two free legs and a second portion at the side of the second end opposite to the first end for accommodating the head, the second portion having a free end and being flexible so as to allow introduction and clamping of the head.

U.S. Pat. No. 9,005,260 (the entire contents of which are incorporated herein by reference) describes a receiver body for an elongated spinal fixation element. The receiver body includes a housing portion with one or more flanges extending outwardly. The receiver body includes first and second flanges extending outwardly from the housing portion. The housing portion in the '260 patent includes first and second slots that form a passage through the housing portion. Each flange has a circular perimeter edge and a chamfered section, the chamfered section having a notched undercut for engagement with an instrument.

U.S. Pat. No. 10,105,162 (the entire contents of which are incorporated herein by reference) describes a spinal fixing device in which a head portion of a bone screw to be inserted into a vertebra is bound to a housing, and the housing is fixed to a spine rod. The spinal fixing device in the '162 patent includes: the housing having a seat portion inside and having a mounting groove for mounting the spine rod; a chuck to be inserted into the seat portion, in which a peripheral portion having an elastically changeable diameter and a curved inner circumferential surface is formed along the circumference of the chuck at one side; and the bone screw having a spherical head portion to be inserted into the peripheral portion.

U.S. Pat. No. 10,524,839 (the entire contents of which are incorporated herein by reference) describes a bone fixation screw apparatus including a bone screw which is inserted to a lower side of a receiving portion and has a spherical head formed at a proximal end, a collect chuck which is inserted to an upper side of the receiving portion to be connected with the spherical head of the bone screw inside the receiving portion, and a rod which is seated on an upper side of the collet chuck and fixed through a fixing screw fastened to the receiving portion, in which the bone screw and the collet chuck are introduced to the receiving portion in opposite directions to each other.

U.S. Pat. No. 8,172,876 (the entire contents of which are incorporated herein by reference) describes a spinal fixation system that includes a coupling member and a locking device that is operable to fix an elongate member relative to the coupling member. In one form, locking device includes opposing lock arms operable to retain the locking device relative to the coupling member in an initial position prior to the locking device fixing the elongate member relative to the coupling member. In another form, the coupling member and locking device include a cooperating structure therebetween in the form of a protrusion and a guide track, the cooperating structure arranged and configured to retain the locking device within an internal space of the coupling member.

U.S. Pat. No. 8,632,571 (the entire contents of which are incorporated herein by reference) describes a pedicle screw that has a screw shaft and a screw head connected thereto. The screw head has a center longitudinal axis extending in an X-direction. The screw further has a recess for receiving a connecting rod with a circular cross-section, a fixing screw that is used to fix the connecting rod in the screw head, a clamping unit between the fixing screw and a head base and an intermediate element.

U.S. Pat. No. 9,848,892 (the entire contents of which are incorporated herein by reference) describes a bone anchoring element that includes a screw having a shank with a bone thread portion and a head. The anchoring element also includes a receiving part for connecting the screw to a rod-shaped element, the screw and the receiving part being connected to one another in a polyaxial or monoaxial manner, and the shank of the screw being of tubular design and its wall having a plurality of recesses.

U.S. Pat. No. 10,716,596 (the entire contents of which are incorporated herein by reference) describes a translating polyaxial bone screw assembly for anchoring a connecting rod to a spinal vertebra. The translating polyaxial bone screw assembly has a bone screw having a threaded shank and a head coupled to a yoke. The yoke has at one end a rod receiving channel for receiving a connecting rod and has an opposite end that is coupled to the bone screw by a coupling assembly. The coupling assembly couples the yoke for polyaxial movement relative to the bone screw and for translational movement of the yoke in a direction transverse to the axis of the bone screw.

SUMMARY OF THE INVENTION

In one embodiment, there is provided a modular screw assembly for use in stabilizing a spinal column. The assembly has a fastener which couples to a screw head of a bone anchor, a screw head coupler, a retaining ring, and a friction ring, wherein the fastener houses the screw head coupler, the retaining ring, and the friction ring and wherein translation of the fastener past the screw head results in the retaining ring elastically deforming and then snapping around the screw head.

In one embodiment, there is provided a system for stabilizing a spinal column. The system has at least one modular screw assembly, at least one bone anchor, a connecting rod, and at least one set screw, wherein the at least one modular screw assembly has a fastener which couples to a screw head of the at least one bone anchor, a screw head coupler, a retaining ring, and a friction ring, and wherein (after securing the modular screw assembly by snapping the retaining ring around the screw head) the connecting rod is fastened to the modular screw assembly by the at least one set screw.

In one embodiment, there is provided a method for stabilizing a spinal column. The method a) attaches a bone anchor to a vertebra of the spinal column, b) translates a modular screw assembly (such as described above) downward onto a head of the bone anchor, c) snaps a retaining ring held in the modular screw assembly around the head of the bone anchor to secure the modular screw assembly to the bone anchor, d) secures a connecting rod to the fastener of the modular screw assembly, and e) locks the modular screw assembly to the head of the bone anchor.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE INVENTION

Surgeons often encounter difficulty in aligning and securing rods to pedicle screws attached to different vertebra for vertebra stabilization because of the limited surgical disc space available for the surgical procedure. Even without unforeseen problems, alignment and attachment of rods to pedicle screws is tedious. A modular screw such as in the present invention allows the surgeon to place the bone anchors, complete his/her work in the disc space, and then snap on the modular screw head and then align and connect the rods to the modular screw head.

Modular Screw Devices of the Invention

In one embodiment of the invention, as noted above, there is provided a system for stabilizing the spinal column. One component of this system is the inventive modular screw assembly detailed below.

Figure 1:
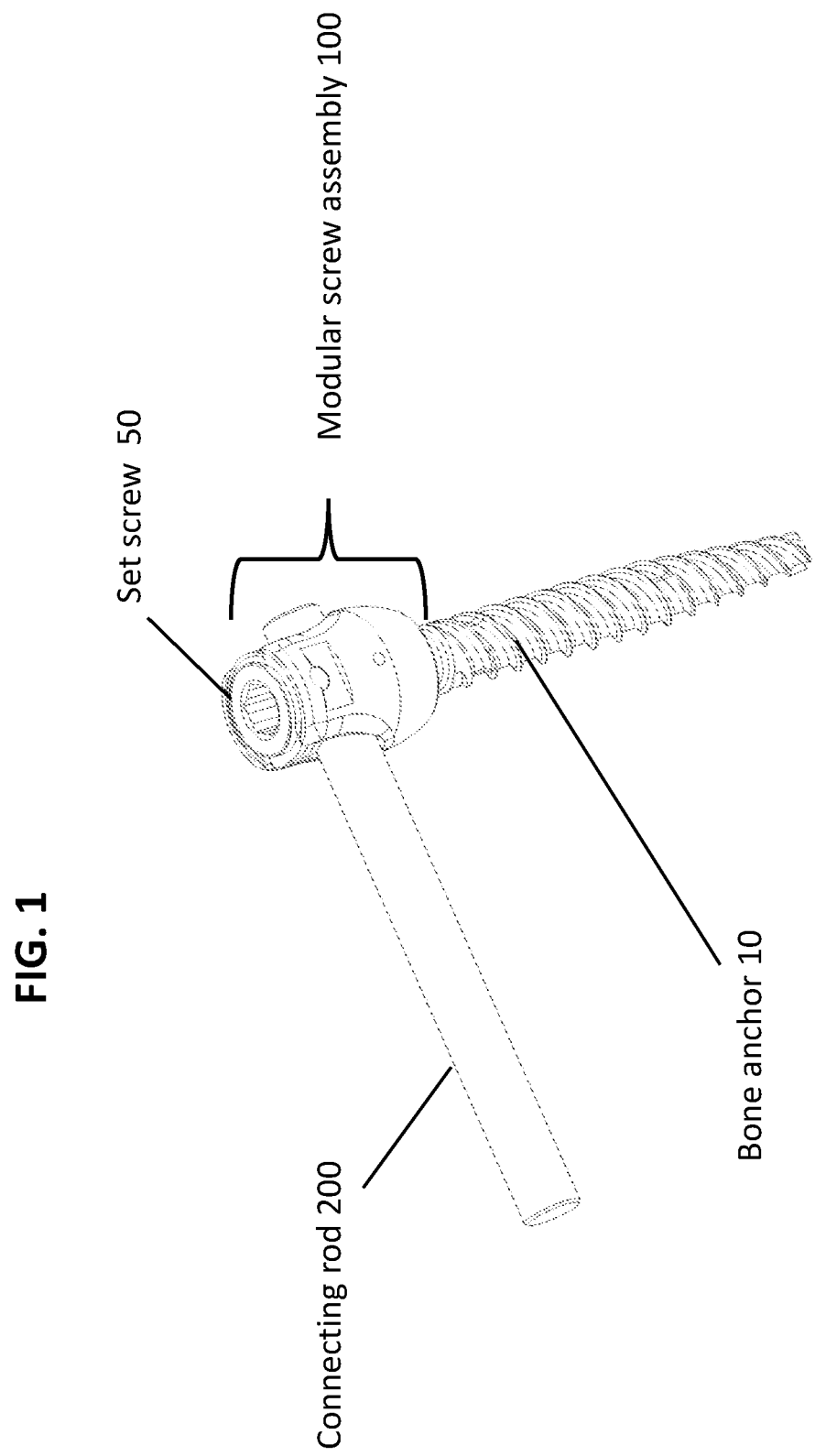
FIG. 1 is a perspective view of a modular screw assembly attached to connecting rod.

FIG. 1 is a perspective view of a modular screw assembly 100 attached to a connecting rod 200. FIG. 1 shows bone anchor 10 which during surgery would be attached to a vertebra in the spinal column. Connecting rod 200 would at some point during the surgery be attached to another modular screw connected to another vertebra in the spinal column. As shown in FIG. 1, the connecting rod 200 is fixed to the modular screw assembly 100 by a set screw 50. In practice, another set screw 50 would be used to secure connecting rod 200 to the modular screw connected to the other vertebra in the spinal column. More details of the components of the modular screw assembly 100 and its use will follow in the descriptions of the embodiments below.

Figure 2:
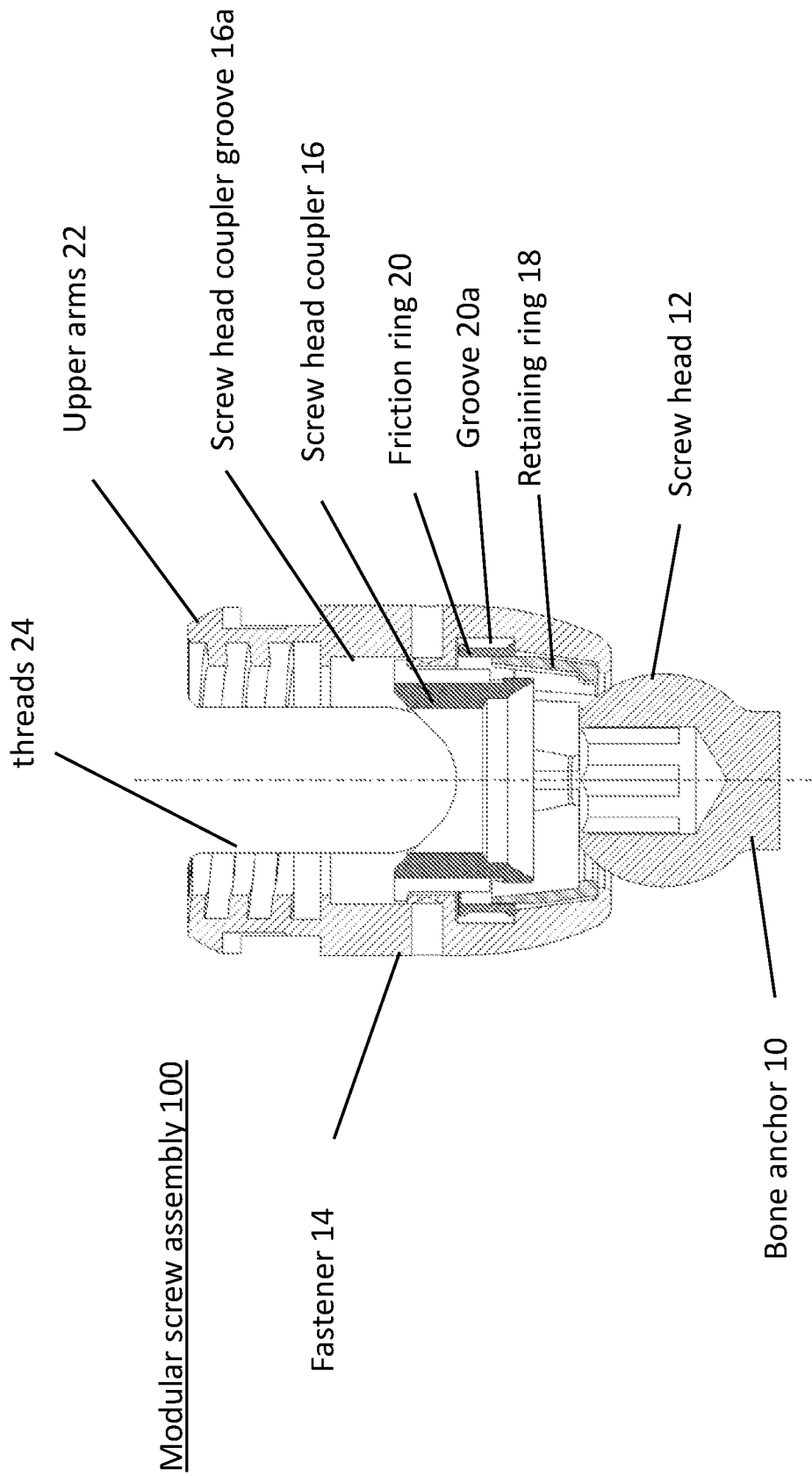
FIG. 2 is an exploded view of the modular screw assembly shown in FIG. 1.

FIG. 2 is an exploded view of the components of modular screw assembly 100. As shown in this embodiment, bone anchor 10 having screw head 12 couples to modular screw assembly 100. Prior to coupling screw head 12 to modular screw assembly 100, bone anchor 10 would be driven (e.g., by rotation) into a vertebra. In one embodiment of the invention, modular screw assembly 100 includes a fastener 14 which couples to screw head 12 through the assistance of screw head coupler 16, retaining ring 18, and friction ring 20.

In one embodiment of the present invention, in operation, the fastener 14, the screw head coupler 16, the retaining ring 18, and the friction ring 20 (as a unit in which fastener 14 holds the screw head coupler 16, the retaining ring 18, and the friction ring 20) are placed onto screw head 12 of bone anchor 10. At this moment, the modular screw assembly is not coupled to bone anchor 10. Next a surgeon would push the modular screw assembly downward, which in turn causes screw head 12 to push into the retaining ring 18, thereby deforming the elastic retaining ring 18. As the surgeon continues to push, the retaining ring 18 slides beyond screw head 12 (elastically deforming) and collapses (or snaps) around screw head 12 (see discussion of FIG. 7 below), thereby connecting the fastener 14, the screw head coupler 16, and the screw head 12 together.

Figure 3:
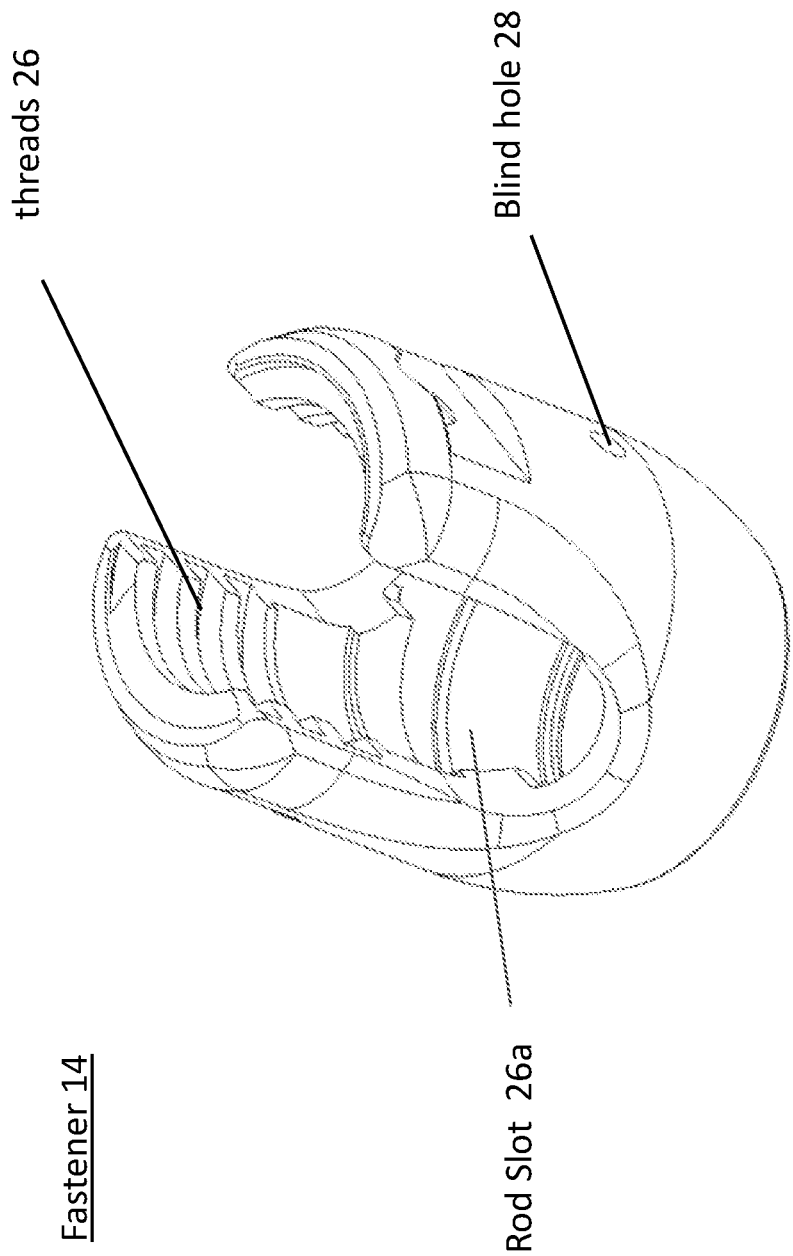
FIG. 3 is a perspective view of a fastener of the modular screw assembly.

FIG. 3 is a perspective view of fastener 14 of modular screw assembly 100. As shown in this embodiment, screw head coupler 16 has a rod seat 24 which accommodates connecting rod 200. Connecting rod 200 pushes screw head coupler 16 downward as the set screw 50 is tightened. Another end of connecting rod 200 would be connected to another modular screw assembly to hold the vertebrae in place.

Figure 4:
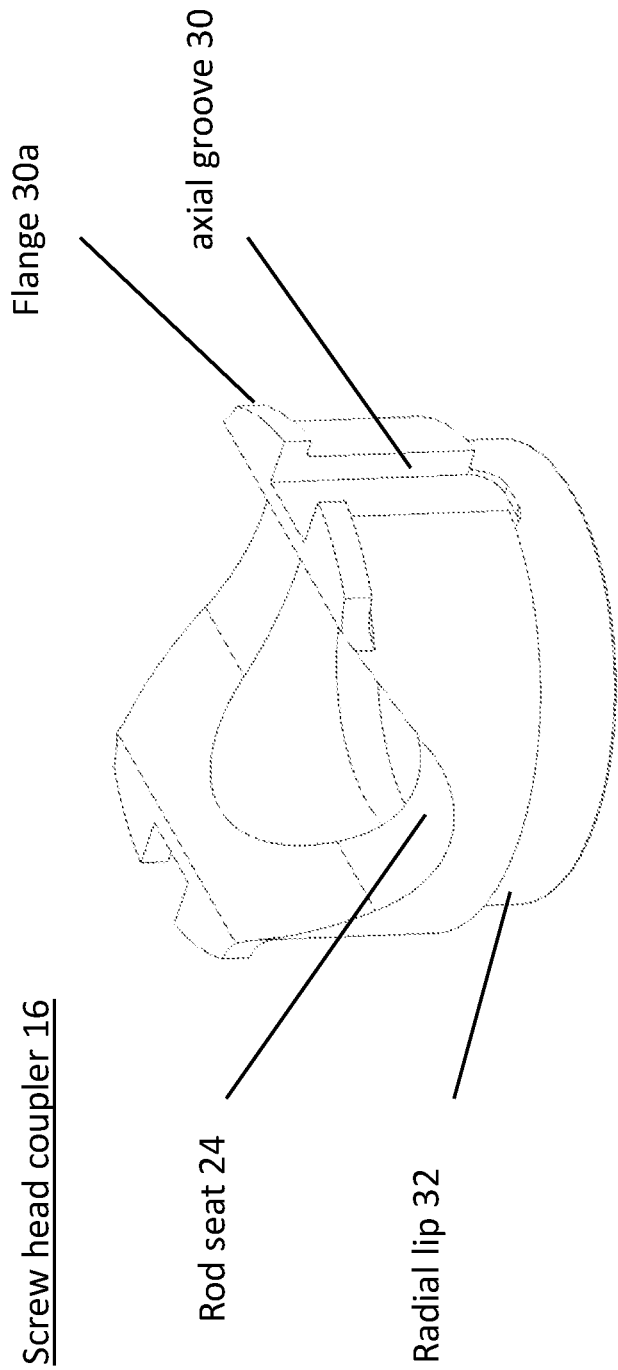
FIG. 4 is a perspective view of a screw head coupler of the modular screw assembly.

FIG. 4 is a perspective view of screw head coupler 16 of modular screw assembly 100. In one embodiment of the invention, modular screw assembly 100 can be locked against rotation by material deformation from a radially extending blind hole 28 on fastener 14 extending inwardly toward the screw head coupler 16. In this embodiment, a remaining section of the fastener 14 at the end of the blind hole 28 is deformable. Deformation of the remaining section of the blind hole 28 pushes material into an axial groove 30 of the screw head coupler 16 to prevent rotation of the screw head holder inside the fastener 14. Prior to deforming the blind hole material, the screw head coupler 16 is inserted from the top of the fastener 14 with the two flanges 30a aligned with rod slots 26a. After the flanges 30a are aligned with screw head coupler groove 16a, the screw head coupler 16 is rotated 90 degrees to align axial groove 30 with the blind hole 28.

In another embodiment of the invention, a radial lip 32 disposed at the lower side of screw head coupler 16 accommodates retaining ring 18. As seen in FIG. 2, inside fastener 14, retaining ring 18 is contained by groove 20a in an interior wall of the fastener 15 and by the radial lip 32

Figure 5:
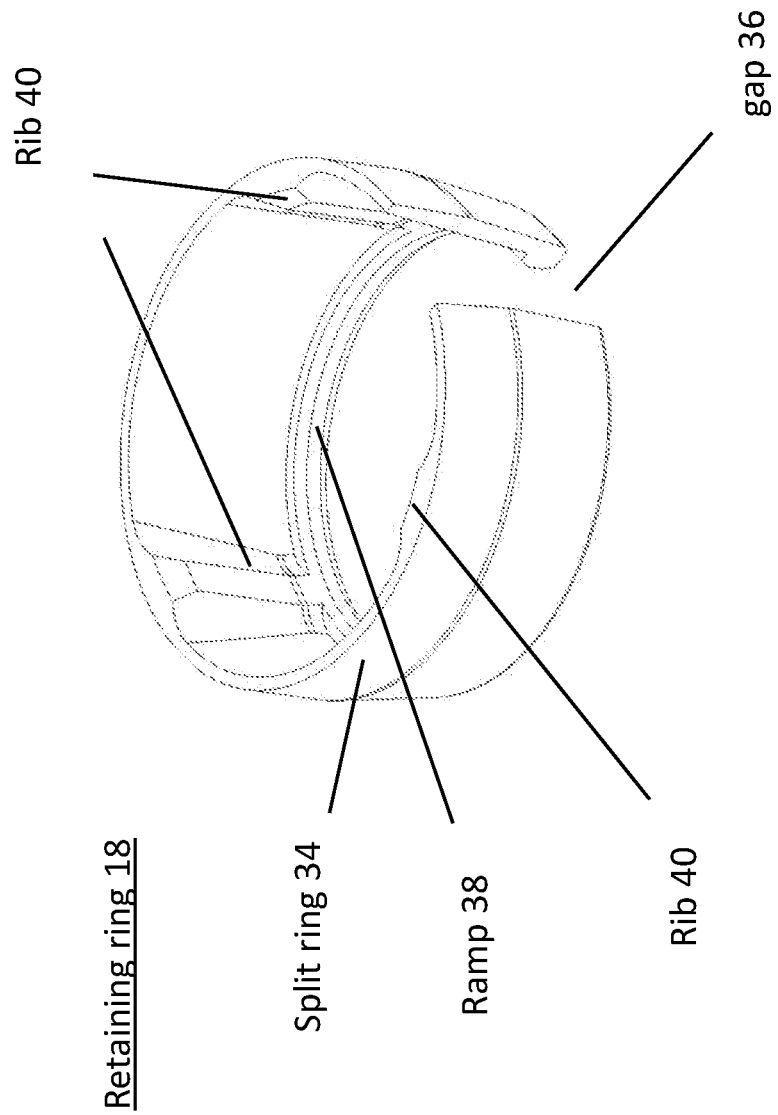
FIG. 5 is a perspective view of a retaining ring of the modular screw assembly.

FIG. 5 is a perspective view of retaining ring 18 of modular screw assembly 100. As shown in FIG. 5, retaining ring 18 comprises a split ring 34 and a gap 36 on its perimeter. In one embodiment of the invention, split ring 34 has a cylindrical interior ramp 38 having a surface which, under pressure from the screw head 12 pushing into retaining ring 18, spreads apart gap 36. With more detail than given above, when the surgeon pushes the modular screw assembly downward, screw head 12 pushes into the retaining ring 18 forcing the split ring 34 to develop a wider gap 36. As the surgeon continues to push, split ring 34 slides beyond head 12 and collapses around screw head 12, thereby connecting the fastener 14, the screw head coupler 16, and the screw head 12 together.

As shown in FIG. 5, in one embodiment of the invention, split ring 34 has ribs 40 disposed at different radial positions around an internal surface of the split ring. The ribs 40 provide for an interference fit stabilizing the screw head 12 to an interior wall of the fastener 14 by way of the ribs intervening between the interior wall and the screw head 12. Friction ring 20 mates with an interference fit to the outer wall of the split ring 34 to further stabilize the split ring 34 in groove 20a (shown in FIG. 2) of fastener 14.

Figure 6:
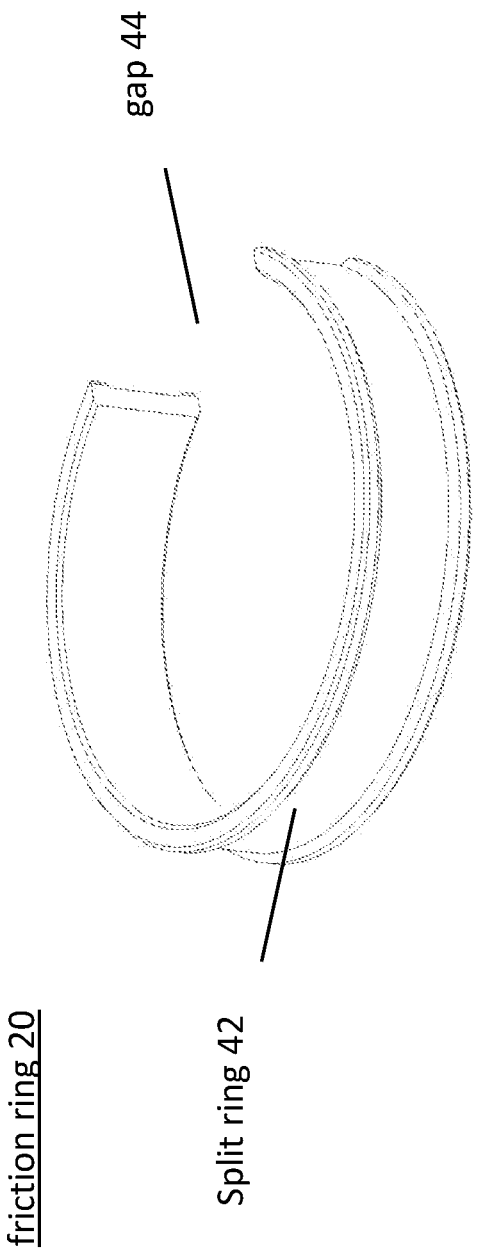
FIG. 6 is a perspective view of a friction ring of the modular screw assembly.

FIG. 6 is a perspective view of friction ring 20 of modular screw assembly 100. As shown in FIG. 6, friction ring 20 (similar to retaining ring 18) comprises a split ring 42 and a gap 44 on its perimeter. Split ring 42, under pressure from the retaining ring 18 as screw head 12 pushes into the retaining ring 18, spreads apart gap 44.

In one embodiment of the present invention, fastener 14 comprises a groove 20a formed in an internal wall to hold friction ring 20 from translational movement. In one embodiment of the present invention, the screw header coupler 16 comprises a radial lip 32 disposed at a lower side of the screw head coupler 16. As detailed above, material deformed from a wall of fastener 14 and pushed into axial groove 30 in the screw head coupler 16 holds the fastener 14 from rotational movement.

In another embodiment of the present invention, after the translation of the fastener 14 past the screw head, the retaining ring 18, and the friction ring 20 are all held in place by interference fitting to the fastener 14. The spherical shaped screw head 12 of bone anchor 10 still allows angular rotation of the fastener 14 relative to the bone anchor 10, but (with the interference fitting) this angular movement occurs only when the friction forces are exceeded In still another embodiment of the present invention, the screw header coupler 16 comprises a radial lip 32 disposed at a lower side of the screw head coupler 16 to accommodate the retaining ring 18, and (after the translation of the fastener past the screw head) the radial lip 32 of the screw head coupler 16, the retaining ring 18, and the friction ring 20 are in compression and thereby held in place by interference fitting to the fastener 14.

In yet another embodiment of the present invention, a set screw 50 for securing a connecting rod 200 to the fastener 16 is provided, and the fastener 16 further comprises a rod seat 24 which is configured to engage connecting rod 200 when the set screw 50 drives the connecting rod 200 downward into the rod seat 24. In this embodiment, interference fitting is increased by screwing the set screw 50 down onto the connecting rod 200 which (in turn) pushes the rod seat 24 downward.

In another embodiment of the present invention, prior to screwing the set screw 50 down onto the connecting rod 200, connecting rod 200 is rotatable for alignment of the connecting rod.

Operation of Modular Screw Assembly

Figure 7:
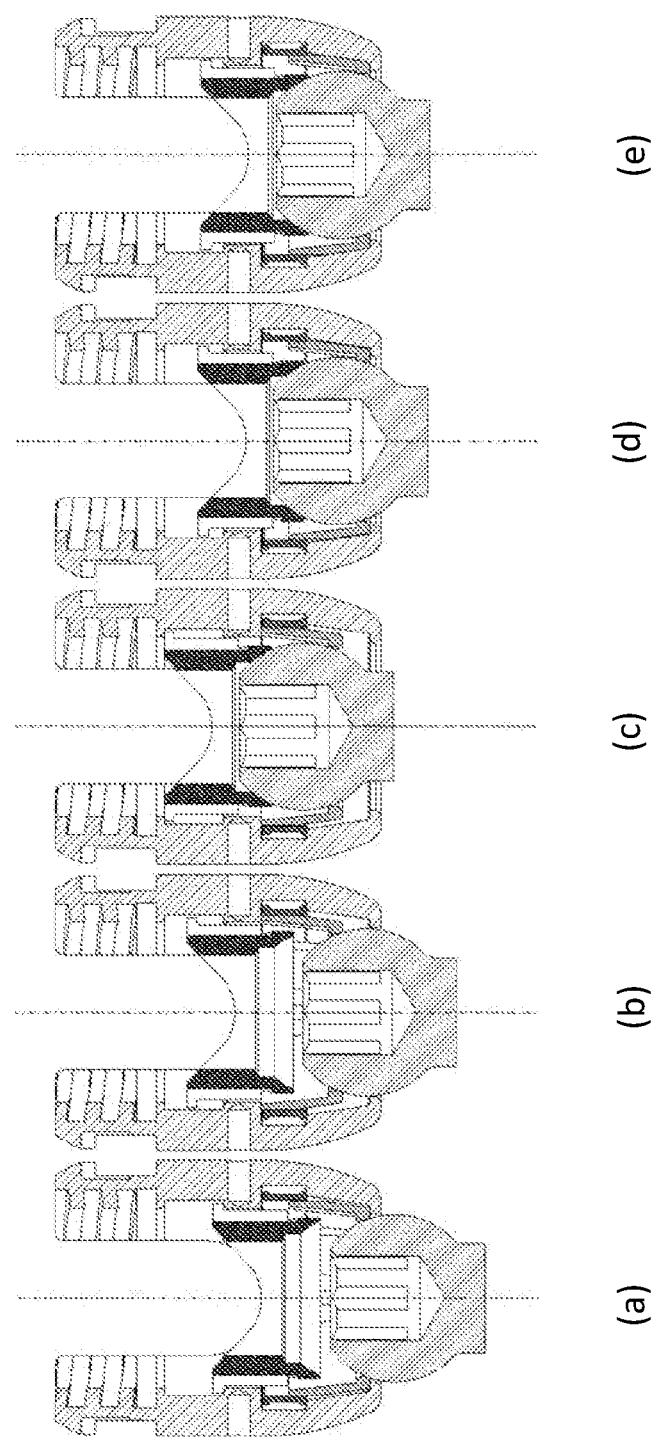
FIG. 7 is a schematic depicting the progression of events leading to securing the modular screw assembly to a bone anchor.

FIG. 7 is a schematic depicting the progression of events leading to securing the modular screw assembly to a bone anchor. At (a), the modular screw assembly 100 is aligned with bone anchor 10. At (b), the surgeon has begun to push down, thereby engaging screw head 12 with the retaining ring 18, thereby starting to spread apart gap 36 and gap 44. Events (c)-(e) show the progression leading to the retaining ring 18 sliding beyond screw head 12 and collapsing (or snapping) around screw head 12, thereby connecting the fastener 14, the screw head coupler 16, and the screw head 12 together.

At this point, the connecting rod 200 can be secured to the modular screw assembly 100 using set screw 50. With the connecting rod 200 attached to one modular screw assembly, the connecting rod may be rotated in all directions as screw head coupler 16 can still rotates around screw heard 12. Once aligned and secured to another modular screw assembly 100, the modular screw assemblies can be locked to the head of the bone anchor (e.g., by screwing the set screw into threads 24 of the fastener 14).

Figure 8:
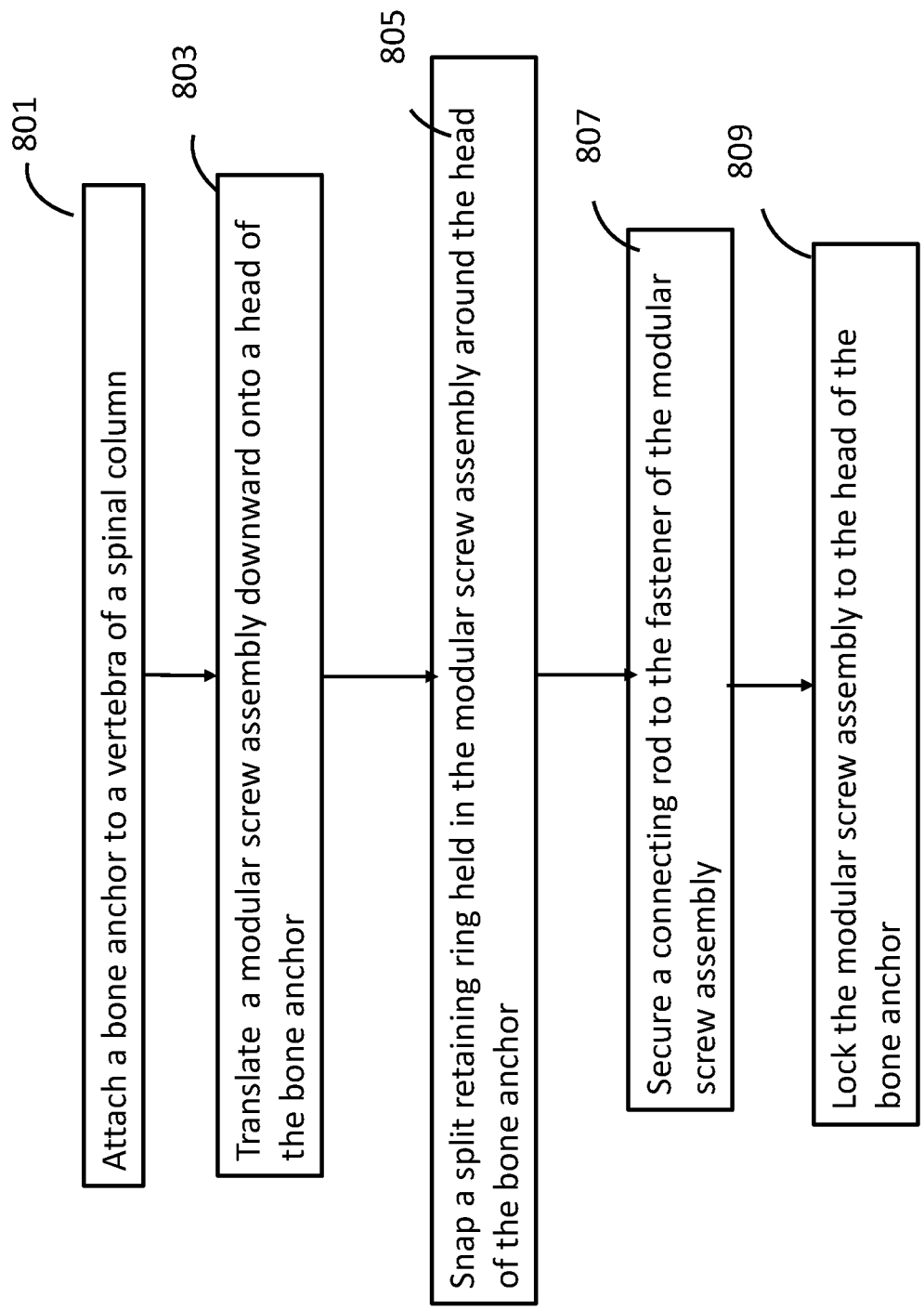
FIG. 8 is a flowchart depicting a method of the invention for orthopedic insertion and expansion of an expandable screw into a bone segment of a patient.

FIG. 8 is a flowchart depicting a method for stabilizing a spinal column. This method at 801 attaches a bone anchor to a vertebra of the spinal column. At 803, the method translates a modular screw assembly (such as described above) downward onto a head of the bone anchor. At 805, a split retaining ring held in the modular screw assembly snaps around the head of the bone anchor. At 807, a connecting rod is secured to the fastener of the modular screw assembly. At 809, the modular screw assembly is locked to the head of the bone anchor (e.g., by screwing the set screw into threads of the fastener).

In some embodiments, any of the screws and instruments described above can be used with additional screws, implants, and instruments. In some embodiments, the implants and instruments can be used with other stabilization members, such as implants, plates, and screws.

STATEMENTS OF THE INVENTION

The following are non-limiting statements of the invention describing various aspects of the invention. However, these statements (and the claims to follow) are not limited to the embodiments depicted in the drawings.

Statement 1. A modular screw assembly for use in stabilizing a spinal column, comprising: a fastener which couples to a screw head of a bone anchor; a screw head coupler; a retaining ring; and a friction ring, wherein the fastener houses the screw head coupler, the retaining ring, and the friction ring, and translation of the fastener past the screw head results in the retaining ring elastically deforming and then snapping around the screw head. In one aspect, the elasticity of the retaining ring acts as a spring member securing the screw head to the screw head coupler.

Statement 2. The assembly of statement 1, wherein the retaining ring comprises a split ring having a gap on a perimeter.

Statement 3. The assembly of any of the statements above, wherein the translation of the fastener by the screw head results in the gap of the split ring expanding until the split ring snaps past the screw head.

Statement 4. The assembly of any of the statements above 2, wherein the retaining ring further comprises an internal ramp which engages the screw head of the bone anchor during the translation.

Statement 5. The assembly of any of the statements above 2, wherein the retaining ring further comprises inwardly protruding ribs angularly disposed around the retaining ring to grip the screw head of the bone anchor after the retaining ring snaps around the screw head.

Statement 6. The assembly of any of the statements above, wherein the friction ring comprises a split ring having a gap on a perimeter.

Statement 7. The assembly of any of the statements above, wherein the translation of the fastener past the screw head results in the gap of the split ring of the friction ring expanding until the retaining ring snaps past the screw head.

Statement 8. The assembly of any of the statements above, wherein the screw head coupler comprises an axial groove, the fastener comprises a blind hole aligned with the axial groove of the screw head coupler, and material deformed from a remaining wall of the fastener beyond the blind hole and pushed into the axial groove of the screw head coupler prevents the fastener and the screw head coupler from relative rotation.

Statement 9. The assembly of any of the statements above, wherein the fastener comprises:

a cylindrical shell housing the screw head coupler, the retaining ring, and the friction ring; and opposing upper arms extending from the cylindrical shell and having threads disposed on an interior of the upper arms for securing a connecting rod to the fastener by a set screw engaging the threads.

Statement 10. The assembly of any of the statements above, further comprises a set screw for securing a connecting rod to the fastener.

Statement 11. The assembly of any of the statements above, wherein the screw head coupler further comprises a rod seat which is configured to engage the connecting rod when the set screw drives the connecting rod downward to the rod seat.

Statement 12. The assembly of any of the statements above, wherein the fastener comprises a groove formed in an internal wall to hold the retaining ring.

Statement 13. The assembly of any of the statements above, wherein the screw header coupler comprises a radial lip disposed at a lower side of the screw head coupler.

Statement 14. The assembly of any of the statements above, wherein the fastener comprises a groove formed in an internal wall to hold the retaining ring from translational movement, the screw header coupler comprises a radial lip disposed at a lower side of the screw head coupler, and material deformed from a remaining wall of the fastener beyond the blind hole and pushed into the axial groove of the screw head coupler prevents the fastener and the screw head coupler from relative rotation.

Statement 15. The assembly of any of the statements above, wherein, after the translation of the fastener past the screw head, the screw head coupler, the retaining ring, and the friction ring are all held in place by interference fitting to the fastener.

Statement 16. The assembly of any of the statements above, wherein the screw header coupler comprises a radial lip disposed at a lower side of the screw head coupler, and after securing the set screw against the rod, the screw head coupler, the retaining ring, and the friction ring are in compression and thereby held in place by the interference fitting to the fastener.

Statement 17. The assembly of any of the statements above, further comprises a set screw for securing a connecting rod to the fastener, and wherein the screw head holder comprises a rod seat which is configured to engage the connecting rod when the set screw drives the connecting rod downward into the rod seat, and the interference fitting is increased by screwing the set screw down onto the connecting rod which pushes the rod seat downward.

Statement 18. The assembly of any of the statements above, wherein, prior to screwing the set screw down onto the connecting rod, the connecting rod is rotatable for alignment of the connecting rod.

Statement 19. A system for stabilizing a spinal column, comprising:
 a modular screw assembly of any of statements 1-18;
 multiple bone anchors;
 a connecting rod; and
 multiple set screws.

Statement 20. The system of statement 19, wherein
 the fastener of statement 1 couples to the screw head of the bone anchor of statement 1, and
 after securing the modular screw assembly of statement 1 by snapping the retaining ring of statement 1 around the screw head, the connecting rod is fastened to the modular screw assembly by at least one of the set screws.

Statement 21. A method for utilizing the modular screw of any of statements 1-18 for stabilization of a spinal column, the method comprising:
 attaching a bone anchor to a vertebra of the spinal column;
 translating a modular screw assembly downward onto a head of the bone anchor;
 snapping a retaining ring, held in the modular screw assembly, around the head of the bone anchor to secure the modular screw assembly to the bone anchor;
 securing a connecting rod to the fastener of the modular screw assembly; and
 locking the modular screw assembly to the head of the bone anchor.

Numerous modifications and variations of the present invention are possible in light of the above teachings. It is therefore to be understood that within the scope of the appended claims, the invention may be practiced otherwise than as specifically described herein.

The invention claimed is:

1. A modular screw assembly for use in stabilizing a spinal column, comprising:
 a fastener which couples to a screw head of a bone anchor;
 a screw head coupler;
 a retaining ring; and
 a friction ring,
 wherein
 the fastener houses the screw head coupler, the retaining ring, and the friction ring,
 translation of the fastener past the screw head results in the retaining ring elastically deforming and then snapping around the screw head, and
 the friction ring mates to an outer wall of the retaining ring such that, upon the translation, the retaining ring slides along an inner surface of the friction ring.

2. The assembly of claim 1, wherein the retaining ring comprises a split ring having a gap on a perimeter.

3. The assembly of claim 2, wherein the translation of the fastener by the screw head results in the gap of the split ring expanding until the split ring snaps past the screw head.

4. The assembly of claim 2, wherein the retaining ring further comprises an internal ramp which engages the screw head of the bone anchor during the translation.

5. The assembly of claim 1, wherein the friction ring comprises a split ring having a gap on a perimeter.

6. The assembly of claim 5, wherein the translation of the fastener past the screw head results in the gap of the split ring of the retaining ring expanding until the retaining ring snaps past the screw head.

7. The assembly of claim 1, wherein
 the screw head coupler comprises an axial groove
 the fastener comprises a blind hole aligned with the axial groove of the screw head coupler, and
 material deformed from a remaining wall of the fastener beyond the blind hole and pushed into the axial groove of the screw head coupler prevents the fastener and the screw head coupler from relative rotation.

8. The assembly of claim 1, wherein the fastener comprises:
 a cylindrical shell housing the screw head coupler, the retaining ring, and the friction ring; and
 opposing upper arms extending from the cylindrical shell and having threads disposed on an interior of the upper arms for securing a connecting rod to the fastener by a set screw engaging the threads.

9. The assembly of claim 1, further comprises a set screw for securing a connecting rod to the fastener.

10. The assembly of claim 9, wherein the screw head coupler comprises a rod seat which is configured to engage the connecting rod when the set screw drives the connecting rod downward to the rod seat.

11. The assembly of claim 1, wherein the fastener comprises a groove formed in an internal wall to hold the retaining ring.

12. The assembly of claim 1, wherein the screw header coupler comprises a radial lip disposed at a lower side of the screw head coupler.

13. The assembly of claim 10, wherein
 the fastener comprises a groove formed in an internal wall to hold the retaining ring from translational movement,
 the screw header coupler comprises a radial lip disposed at a lower side of the screw head coupler, and
 material deformed from a remaining wall of the fastener beyond the blind hole and pushed into the axial groove of the screw head coupler prevents the fastener and the screw head coupler from relative rotation.

14. The assembly of claim 13, wherein, after the translation of the fastener past the screw head, the screw head coupler, the retaining ring, and the friction ring are all held in place by interference fitting to the fastener.

15. The assembly of claim 13, wherein
 the screw header coupler comprises a radial lip disposed at a lower side of the screw head coupler, and
 after securing the set screw against the rod, the screw head coupler, the retaining ring, and the friction ring are in compression and thereby held in place by the interference fitting to the fastener.

16. The assembly of claim 15, further comprises a set screw for securing a connecting rod to the fastener, and wherein
 the screw head holder comprises a rod seat which is configured to engage the connecting rod when the set screw drives the connecting rod downward into the rod seat, and the interference fitting is increased by screwing the set screw down onto the connecting rod which pushes the rod seat downward.

17. The assembly of claim 16, wherein, prior to screwing the set screw down onto the connecting rod, the connecting rod is rotatable for alignment of the connecting rod.

18. A method for utilizing the modular screw assembly of claim 1 for stabilization of a spinal column, the method comprising:
attaching a bone anchor to a vertebra of the spinal column;
translating the modular screw assembly downward onto a head of the bone anchor;
snapping the retaining ring of claim 1, held in the modular screw assembly, around the head of the bone anchor to secure the modular screw assembly to the bone anchor;
securing a connecting rod to the fastener of the modular screw assembly; and
locking the modular screw assembly to the head of the bone anchor.

19. The assembly of claim 1, wherein an upper end of the retaining ring overlaps with the friction ring in a direction of the translation.

20. A modular screw assembly for use in stabilizing a spinal column, comprising:
a fastener which couples to a screw head of a bone anchor;
a screw head coupler;
a retaining ring; and
a friction ring,
wherein
the fastener houses the screw head coupler, the retaining ring, and the friction ring,
translation of the fastener past the screw head results in the retaining ring elastically deforming and then snapping around the screw head, wherein the retaining ring comprises a split ring having a gap on a perimeter and further comprises inwardly protruding ribs angularly disposed around the retaining ring to grip the screw head of the bone anchor after the retaining ring snaps around the screw head, and
the inwardly protruding ribs extend along a direction of the translation.

21. A system for stabilizing a spinal column, comprising:
at least one modular screw assembly;
at least one bone anchor;
a connecting rod; and
at least one set screw,
wherein
the at least one modular screw assembly has a fastener which couples to a screw head of the at least one bone anchor, a screw head coupler, a retaining ring, and a friction ring,
after securing the at least one modular screw assembly by snapping the retaining ring around the screw head, the connecting rod is fastened to the modular screw assembly by the at least one set screw, and
the friction ring mates to an outer wall of the retaining ring such that, upon translation of the fastener past the screw head, the retaining ring slides along an inner surface of the friction ring resulting in the retaining ring elastically deforming and then snapping around the screw head.

* * * * *